US008524929B2

(12) United States Patent
Kale et al.

(10) Patent No.: US 8,524,929 B2
(45) **Date of Patent: *Sep. 3, 2013**

(54) EXTRACTION WITH FRACTIONATION OF LIPIDS AND PROTEINS FROM OLEAGINOUS MATERIAL

(71) Applicant: Arizona Board of Regents for and on behalf of Arizona State University, Scottsdale, AZ (US)

(72) Inventors: Aniket Kale, Chandler, AZ (US); Qiang Hu, Chandler, AZ (US); Milton Sommerfeld, Chandler, AZ (US)

(73) Assignee: Arizona Board of Regents for and on behalf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/653,595

(22) Filed: Oct. 17, 2012

(65) Prior Publication Data

US 2013/0041168 A1 Feb. 14, 2013

Related U.S. Application Data

(63) Continuation of application No. 13/493,586, filed on Jun. 11, 2012, now Pat. No. 8,318,963, which is a continuation of application No. 13/273,159, filed on Oct. 13, 2011, now Pat. No. 8,222,437, which is a continuation of application No. 13/116,602, filed on May 26, 2011, now Pat. No. 8,212,060, which is a continuation of application No. PCT/US2011/031353, filed on Apr. 6, 2011.

(60) Provisional application No. 61/321,286, filed on Apr. 6, 2010.

(51) Int. Cl.

| | |
|---|---|
| ***C09F 1/02*** | (2006.01) |
| ***B01D 11/04*** | (2006.01) |
| ***C12P 7/64*** | (2006.01) |
| ***A61K 36/02*** | (2006.01) |

(52) U.S. Cl.
USPC ............. 554/20; 210/633; 210/634; 435/134; 530/370

(58) Field of Classification Search
USPC ................... 554/20; 210/633, 634; 435/134; 530/370
See application file for complete search history.

(56) References Cited

U.S. PATENT DOCUMENTS

| | | | | |
|---|---|---|---|---|
| 1,689,277 | A | 10/1928 | Burns | |
| 3,850,802 | A | 11/1974 | Berger | |
| 3,850,807 | A | 11/1974 | Jones | |
| 3,856,569 | A | 12/1974 | Strong | |
| 3,875,052 | A | 4/1975 | Lonchamp et al. | |
| 4,062,882 | A | 12/1977 | Sen Gupta | |
| 4,264,452 | A | 4/1981 | Chen | |
| 4,341,038 | A | 7/1982 | Bloch et al. | |
| 4,439,629 | A | 3/1984 | Ruegg | |
| 4,787,981 | A | 11/1988 | Tanahashi et al. | |
| 5,130,242 | A | 7/1992 | Barclay | |
| 5,198,111 | A | 3/1993 | Davis | |
| 5,338,673 | A | 8/1994 | Thepenier et al. | |
| 5,374,657 | A | 12/1994 | Kyle | |
| 5,378,369 | A | 1/1995 | Rose et al. | |
| 5,440,028 | A | 8/1995 | Buchholz et al. | |
| 5,539,133 | A | 7/1996 | Kohn et al. | |
| 5,545,329 | A | 8/1996 | LaMonica | |
| 5,569,383 | A | 10/1996 | Vander Ark, Jr. et al. | |
| 5,658,767 | A | 8/1997 | Kyle | |
| 5,804,072 | A | 9/1998 | Yang | |
| 6,000,551 | A | 12/1999 | Kanel et al. | |
| 6,166,231 | A | 12/2000 | Hoeksema | |
| 6,180,376 | B1 | 1/2001 | Liddell | |
| 6,267,879 | B1 | 7/2001 | Gil | |
| 6,372,460 | B1 | 4/2002 | Gladue et al. | |
| 6,443,312 | B1 | 9/2002 | Racine | |
| 6,524,486 | B2 | 2/2003 | Borodyanski et al. | |
| 6,579,714 | B1 | 6/2003 | Hirabayashi et al. | |
| 6,750,048 | B2 | 6/2004 | Ruecker et al. | |
| 6,861,004 | B2 | 3/2005 | Benenson, Jr. et al. | |
| 7,001,505 | B2 | 2/2006 | Hersh | |
| 7,148,366 | B2 | 12/2006 | Cheryan | |
| 7,678,931 | B2 | 3/2010 | Fichtali et al. | |
| 7,695,626 | B2 | 4/2010 | Dueppen et al. | |
| 7,816,570 | B2 | 10/2010 | Roberts, IV et al. | |
| 7,868,195 | B2 | 1/2011 | Fleischer et al. | |
| 8,222,437 | B2 * | 7/2012 | Kale et al. | 554/20 |
| 8,318,963 | B2 * | 11/2012 | Kale et al. | 554/20 |
| 2002/0009493 | A1 | 1/2002 | Schwendeman et al. | |
| 2004/0131580 | A1 | 7/2004 | Hagino et al. | |
| 2005/0161392 | A1 | 7/2005 | Duby | |
| 2005/0164192 | A1 | 7/2005 | Graham et al. | |
| 2005/0170479 | A1 | 8/2005 | Weaver et al. | |
| 2006/0122410 | A1 | 6/2006 | Fichtali et al. | |
| 2007/0025976 | A1 | 2/2007 | Kluetz et al. | |

(Continued)

FOREIGN PATENT DOCUMENTS

| | | |
|---|---|---|
| CA | 2 249 103 | 4/1999 |
| EP | 1 057 833 A1 | 12/2000 |

(Continued)

OTHER PUBLICATIONS

"Algae Oil Extraction," Diversified Technologies, Inc., Bioscience Technology, Jan. 3, 2011 New Source Web Content—US, document also available from: www.ea.gov.au/atmosphere/transport/biodiesel/index.html (1 page).

(Continued)

*Primary Examiner* — Bernard Dentz

(74) *Attorney, Agent, or Firm* — Wilmer Cutler Pickering Hale and Dorr LLP

(57) ABSTRACT

Systems and methods for extracting lipids of varying polarities from oleaginous material.

19 Claims, 9 Drawing Sheets

(56) References Cited

U.S. PATENT DOCUMENTS

| | | | |
|---|---|---|---|
| 2008/0038290 A1 | 2/2008 | Renimel et al. |
| 2008/0118964 A1 | 5/2008 | Huntley et al. |
| 2008/0155888 A1 | 7/2008 | Vick et al. |
| 2008/0160593 A1 | 7/2008 | Oyler |
| 2009/0029445 A1 | 1/2009 | Eckelberry et al. |
| 2009/0148918 A1 | 6/2009 | Trimbur et al. |
| 2009/0148931 A1 | 6/2009 | Wilkerson et al. |
| 2009/0162919 A1 | 6/2009 | Radaelli et al. |
| 2009/0181463 A1 | 7/2009 | Chen |
| 2009/0234146 A1 | 9/2009 | Cooney et al. |
| 2010/0055741 A1 | 3/2010 | Galvez, III et al. |
| 2010/0068772 A1 | 3/2010 | Downey |
| 2010/0196971 A1 | 8/2010 | Lin et al. |
| 2010/0233761 A1 | 9/2010 | Czartoski et al. |
| 2010/0261922 A1 | 10/2010 | Fleischer et al. |
| 2010/0317088 A1 | 12/2010 | Radaelli et al. |
| 2011/0086386 A1 | 4/2011 | Czartoski et al. |
| 2011/0124034 A1 | 5/2011 | Kuehnle et al. |
| 2011/0192073 A1 | 8/2011 | Kale |
| 2011/0192075 A1 | 8/2011 | Kale |
| 2011/0195085 A1 | 8/2011 | Kale |
| 2011/0195484 A1 | 8/2011 | Kale |
| 2011/0195485 A1 | 8/2011 | Kale |
| 2011/0196131 A1 | 8/2011 | Kale |
| 2011/0196132 A1 | 8/2011 | Kale |
| 2011/0196135 A1 | 8/2011 | Kale |
| 2011/0253605 A1 | 10/2011 | Hu et al. |
| 2011/0253612 A1 | 10/2011 | Kale et al. |
| 2011/0253646 A1 | 10/2011 | Hu et al. |
| 2011/0258920 A1 | 10/2011 | Licamele et al. |
| 2011/0263883 A1 | 10/2011 | Kale et al. |
| 2011/0263886 A1 | 10/2011 | Kale |

FOREIGN PATENT DOCUMENTS

| | | | |
|---|---|---|---|
| EP | 1 920 777 | A1 | 5/2008 |
| EP | 2 030 626 | A1 | 3/2009 |
| KR | 10-2006-0097947 | | 9/2006 |
| WO | WO-2006/095964 | A1 | 9/2006 |
| WO | WO-2008/031092 | A3 | 3/2008 |
| WO | WO-2008/060571 | A2 | 5/2008 |
| WO | WO-2008/144583 | A1 | 11/2008 |
| WO | WO-2009/082696 | A1 | 7/2009 |
| WO | WO-2009/158658 | A2 | 12/2009 |
| WO | WO-2010/036334 | A1 | 4/2010 |
| WO | WO-2010039030 | A1 | 4/2010 |
| WO | WO-2010/120939 | A2 | 10/2010 |
| WO | WO-2010/123903 | A1 | 10/2010 |
| WO | WO-2010/132414 | A1 | 11/2010 |
| WO | WO-2010/138620 | A1 | 12/2010 |
| WO | WO-2010/151606 | A1 | 12/2010 |
| WO | WO-2011003024 | A2 | 1/2011 |
| WO | WO-2011127127 | | 10/2011 |
| WO | WO-2012024340 | A2 | 2/2012 |

OTHER PUBLICATIONS

Agboola, S. et al., "Characterisation and functional properties of Australian rice protein isolates," Journal of Cereal Science 41 (2005) 283-290.

Amin, S. "Review on biofuel oil and gas production processes from microalgae," Energy Conversion and Management 50 (2009) 1834-1840.

Berberoglu, H. et al., "Radiation characteristics of Chlamydomonas reinhardtii CC125 and its truncated chlorophyll antenna transformants tla1, tlaX and tla1-CW+" International Journal of Hydrogen Energy 33 (2008) 6467-6483.

Bligh, E.G. et al., "A Rapid Method of Total Lipid Extraction and Purification, Canadian Journal of Biochemistry and Physiology," vol. 37, Aug. 1959, No. 8, pp. 911-917.

Borowitzka, M.A. "Commercial production of microalgae: ponds, tanks, tubes and ferments," Journal of Biotechnology 70 (1999) 313-321.

Brennan, L. et al., "Biofuels from microalgae—A review of technologies for production, processing, and extractions of biofuels and co-products," Renewable and Sustainable Energy Reviews 14 (2010) 557-577.

Catchpole, O.J. et al. "The extraction and fractionation of specialty lipids using near critical fluids," J. of Supercritical Fluids 47 (2009) 591-597.

Chisti, Y. "Biodiesel from microalgae," Biotechnology Advances 25 (2007) 294-306.

Christie, W.W., Lipid Analysis, 3rd ed., Oily Press, Bridgewater, UK, 2003, pp. 97-102.

Cooney, et al., "Extraction of Bio-Oils from Microalgae," Separation and Purification Reviews, vol. 38(4): 291-325 (Oct. 1, 2009).

Communication Relating to the Results of the Partial International Search for corresponding International Patent Application No. PCT/US2011/031412 mailed Aug. 9, 2011 (12 pages).

International Search Report and Written Opinion for International Patent Application No. PCT/US2011/031404 mailed Aug. 3, 2011. 14 pages.

International Search Report and Written Opinion for International Patent Application No. PCT/US2011/031407 mailed Aug. 9, 2011. 12 pages.

International Search Report and Written Opinion for International Patent Application No. PCT/US2011/031408 mailed Aug. 9, 2011.

International Search Report and Written Opinion for International Patent Application No. PCT/US2011/031414 mailed Aug. 5, 2011. 13 pages.

International Search Report and Written Opinion for International Patent Application No. PCT/US2011/031417 mailed Aug. 3, 2011. 13 pages.

International Search Report and Written Opinion for International Patent Application No. PCT/US2011/031419 mailed Sep. 5, 2011. 15 pages.

International Search Report and Written Opinion for International Patent Application No. PCT/US2011/031421 mailed Aug. 3, 2011. 13 pages.

U.S. Appl. No. 13/116,602, filed May 26, 2011. 34 pages.

U.S. Appl. No. 13/116,610, filed May 26, 2011. 34 pages.

U.S. Appl. No. 13/149,463, filed May 31, 2011. 38 pages.

U.S. Appl. No. 13/149,524, filed May 31, 2011. 13 pages.

U.S. Appl. No. 13/149,531, filed May 31, 2011. 13 pages.

U.S. Appl. No. 13/149,595, filed May 31, 2011. 85 pages.

Daigger, G.T. et al., "Are Membrane Bioreactors Ready for Wide-spread Application?" Environmental Sciene & Technology, Oct. 1, 2005, pp. 399A-406A. 9 pages.

Database WPI, Week 200326, Thomson Scientific, London, GB; AN 2003-259841 & JP 2002 220402 A (Oriental Bio KK) Aug. 9, 2002, abstract. 2 pages.

de Morais Coutinho, C. et al., "State of art of the application of membrane technology to vegetable oils: A review," Food Research International 42 (2009) 536-550.

Fajardo, A.Rm. et al., "Lipid Extraction from the microalga Phaeodactylum Tricornutum," Eur. J. Lipid Sci. Technol., 109: 120-126 (2007).

Grima, E.M. et al., "Recovery of microalgal biomass and metabolites: process options and economics," Biotechnology Advances 20 (2003) 491-515.

Harun, R. et al., "Bioprocess engineering of microlagae to produce a variety of consumer products," Renewable and Sustainable Energy Reviews 14 (2010) 1037-1047.

Hejazi, M.A. et al., "Milking of microalgae," Trends in Biotechnology vol. 22, No. 4, Apr. 2004, pp. 189-194.

Herfindal, L. et al., "A high proportion of Baltic Sea benthic cynaobacterial isolates contain apoptogens able to induce rapid death of isolated rat hepatocytes," Toxicon 46 (2005) 252-260.

Herrero, M. et al., "Sub- and supercritical fluid extraction of functional ingredients from different natural sources: Plants, food-by-products, algae and microalgae—A Review," Food Chemistry 98 (2006) 136-148.

Huang, G. et al., "Biodiesel production by microalgal biotechnology," Applied Energy 87 (2010) 38-46.

Huang, G. et al., "Rapid screening method for lipid production in alga based on Nile red fluorescence," Biomass and Bioenergy 33 (2009) 1386-1392.

International Search Report issued for PCT/US2011/031353, dated Jan. 2, 2012 (2 pages).
Ju, Z.Y. et al., "Extraction, Denaturation and Hydrophobic Properties of Rice Flour Proteins," Journal of Food Science, vol. 66, No. 2, 2001, pp. 229-232.
Kanda, H. and Li., P. "Simple extraction method of green crude from natural blue-green microalgae by dimethyl ether," Fuel, 90: 1264-1266 (2011).
Knuckey, R.M. et al., "Production of microalgal concentrates by flocculation and their assessment as aquaculture feeds," Aquaculural Engineering 35 (2006) 300-313.
Koris, A. et al., "Dry degumming of vegetable oils by membrane filtration," Desalination 148 (2002) 149-153.
Kumari, P. et al., "Tropical marine macroalgae as potential sources of nutritionally important PUFAs," Food Chemistry 120 (2010) 749-757.
Lee, J-Y., et al., "Comparison of several methods for effective lipid extraction from microalgae," Bioresource Technology, vol. 101: S75-S77 (2010).
Lee, M. et al., "Isolation and Characterization of a Xanthophyll Aberrant Mutant of the Green Alga Nannochloropsis oculata," Marine Biotechnology, 2006, pp. 238-245.
Mata, Teresa M. et al., "Microalgae for biodiesel production and other applications: A review," Renewable and Sustainable Energy Reviews (2009), 16 pages.
Mercer, P. et al., "Developments in oil extraction from microalgae," Eur. J. Lipid Sci. Technol. 2011, 113, 539-547.
Plaza, M. et al., "Screening for bioactive compounds from algae," Journal of Pharmaceuticals and Biomedical Analysis 51 (2010) 450-455.
Ramirez, A. et al., "Lipid extraction from the microalga Phaeodactylum tricornutum," Eur. J. Lipid. Technol. 109 (2007) 120-126.
Raynie, D.E., "Modern Extraction Techniques," Anal. Chem. 2006, 78, 3997-4003.
Rhodes, C.J. "Oil from algae; salvation from peak oil?" Science Progress (2009), 92(1), 39-90.
Rittmann, B.E. "Opportunities for Renewable Bioenergy Using Microorganisms," Biotechnology and Bioengineering, vol. 100, No. 2, Jun. 1, 2008, pp. 203-212.
Rittmann, B.E. et al., Environmental Biotechnology: Principles and Applications. McGraw-Hill Book Co., New York, pp. 24-34, 45, 57, 353-378. (2001).
Rossignol, N. et al., "Membrane technology for the continuous separation microalgae/culture medium: compared performances of cross-flow microfiltration and ultrafiltration," Aquacultutal Engineering 20 (1999) 191-208.
Ryckebosch, E. et al., "Optimization of an Analytical Procedure for Extraction of Lipids from Microalgae," J. Am. Oil Chem. Soc., vol. 89: 189-198 (2012).
Shahidi, "Extraction and Measurement of Total Lipids," Curr. Protocols in Food Analy. Chemistry, John Wiley & Sons, D1.1.1-D.1.11 (2001).
Sostaric, M. et al., "Growth, lipid extraction and thermal degradation of the microalga Chlorella vulgaris," New Biotech., vol. 29(3): 325-331 (Feb. 2012).
Spolaore, P. et al. "Commercial Applications of Microalgae," Journal of Bioscience and Bioengineering, vol. 101, No. 2, 87-96, 2006.
Steinitz, Y. et al., "A Mutant of the Cyanobacterium Plectonema Boryanum Resistant to Photooxidation," Plant Science Letters, vol. 16, Issue 2-3, p. 327-335, Oct. 1979.
Uduman, N. et al. "Dewatering of microalgal cultures: A major bottleneck to algae-based fuels," Journal of Renewable and Sustainable Energy 2, 2010, 012701-1-012701-15.
Voorhees, K.J. et al., "Analysis of Insoluble Carbonaceous Materials from Airborne Particles Collected in Pristine Region of Colorado," Journal of Analytical and Applied Pyrolysis, 18 (1991) 189-205.
Wachowicz, M. et al. "The protein of the alga Spirulina platensis. (translated)." Database FSTA [Online] International Food Information Service (IFIS), Frankfurt-Main, DE; 1974. 1 page.
Webvitamins (2011, updated) "Globulin Protein Concentrate", www.webvitamins.com/Nutrient.aspx?id=2007, 1 page, Author Unknown.

* cited by examiner

EXTRACTION WITH FRACTIONATION OF LIPIDS AND PROTEINS FROM OLEAGINOUS MATERIAL

CROSS-REFERENCE TO RELATED APPLICATION

This application is a continuation of and claims priority to U.S. patent application Ser. No. 13/493,586, filed Jun. 11, 2012, which is a continuation of and claims priority to U.S. patent application Ser. No. 13/273,159, filed Oct. 13, 2011, now U.S. Pat. No. 8,222,437, which is a continuation of and claims priority to U.S. patent application Ser. No. 13/116,602, filed May 26, 2011, now U.S. Pat. No. 8,212,060, which is a continuation of and claims priority to PCT/US2011/031353, filed Apr. 6, 2011, which claims priority to U.S. Provisional Patent Application Ser. No. 61/321,286, filed Apr. 6, 2010, the entireties of which are incorporated herein by reference.

BACKGROUND OF THE INVENTION

A. Field of the Invention

Embodiments of the present invention relate generally to systems and methods for extracting lipids of varying polarity from a wet oleaginous material, including for example, an algal biomass. In particular, embodiments of the present invention concern the ability to both extract & fractionate the algae components by doing sequential extractions with a hydrophilic solvent/water mixture that becomes progressively less polar (i.e. water in solvent/water ratio is progressively reduced as one proceed from one extraction Step to the next). In other words, the interstitial solvent in the algae (75% of its weight) is water initially and is replaced by the polar solvent gradually to the azeotrope of the organic solvent. This results in the extraction of components soluble in the polarity developed at each step, thereby leading to simultaneous fractionation of the extracted components.

B. Description of Related Art

Algae have gained significant importance in the recent years given their inherent advantage in solving several critical issues of the world such as producing renewable fuels, reducing global climate change, wastewater treatment and sustainability. Algae's superiority as a biofuel feedstock arises from a variety of factors, viz, high per-acre productivity compared to typical terrestrial oil crop plants, non-food based feedstock resources, use of otherwise non-productive, non-arable land, utilization of a wide variety of water sources (fresh, brackish, saline, and wastewater), production of both biofuels and valuable co-products. However, the ability to easily recover and fractionate the various oil/byproducts produced by algae is critical to the economic success of the algae oil process.

Several thousand species of algae have been screened and studied for lipid production worldwide over the past several decades of which about 300 rich in lipid production have been identified. The lipids produced by algae are similar in composition compared to the contemporary oil sources such as oil seeds, cereals, and nuts. The lipid composition and content vary at different stages of the life cycle and are affected by environmental and culture conditions. Given considerable variability in biochemical composition and the physical properties of the algae cell wall, the strategies and approaches for extraction are rather different depending on individual algal species/strains employed. The conventional physical extraction processes such as extrusion, do not work well with algae given the thickness of the cell wall and the small size (2~20 nm) of algal cells. Further, the large amounts of polar lipids in the algal oil compared to the typical oil seeds lead to refining issues. However, this can be a great opportunity to recover large amounts of polar lipids which have an existing market and add value to the process.

Typical algal concentration in the culture upon harvesting is about 0.1~1.0% (w/v), thereby requiring the process to remove as high as 1000 times the amount of water to process a unit weight of algae. Conventional or the currently existing oil extraction methods for oleagenous materials strictly require almost completely dry biomass or feed to improve the yield and quality of the oil extracted, thereby rendering the feed to the biofuels process uneconomical and energy-intensive. The feed is extruded or flaked at high temperatures to enhance the extraction. These steps may not work with the existing equipment due to the single cell micrometric nature of algae. Algal oil extraction can be classified as disruptive and non-disruptive methods. Disruptive methods involve cell lysis by mechanical (see U.S. Pat. No. 6,750,048), thermal, enzymatic or chemical methods. Most disruptive methods result in emulsions and require an expensive cleanup process. Algal oils contain a large percentage of polar lipids and proteins which enhance the emulsification of the neutral lipids further stabilized by the nutrient and salt components left in the solution. The resulting oil is a complex mixture requiring an extensive refining process to obtain neutral lipids (feed for conversion to biofuels).

Non-Disruptive methods provide low yields. Milking is a variant of the proposed process. However, it may not work with some species of algae due to solvent toxicity and cell wall disruption. A specific process may be required for each algal strain, mutant and genetic modified organism. Further, the volumes of solvents required would be astronomical due to the maximum attainable concentration in the medium. Multiphase extractions {see U.S. Pat. No. 6,166,231) will require extensive distillations with complex solvent mixtures for solvent recovery and recycle.

The proposed non-disruptive alcoholic extraction process results in over 90% extraction efficiency, and the small amount of polar lipids in the remaining biomass enhances its value. In addition, ethanol extracts can further be directly transesterified. Furthermore, it is a generic process for any algae, and recovers all the valuable components (polar lipids) in the algae with a gradient in alcohol-water mixture. The neutral lipids fraction has a low metal content to start with, thereby enhancing the stability and improving process economics in the subsequent steps.

The proposed system and methods start with wet biomass, reducing the dying and dewatering costs. Compared to the contemporary processes, this process should have a relatively low operating cost due to the moderate temperature and pressure conditions along with the solvent recycle. In addition, continuous solvent extraction is a proven technology, and chlorophylls may be removed from the fuel-lipid fractions by solvent and solid interactions. Furthermore, the existing processes are cost prohibitive and cannot meet the demand of the market.

Another aspect of proposed systems and methods is the ability to separate the polar lipids from neutral lipids during the extraction process. The polar lipids along with metals result in processing difficulties for separation and utilization of neutral lipids. We take this opportunity to develop a value added aspect to the extraction process and at the same time separate the polar lipids. The polar lipids are surfactants by nature due to their molecular structure. The world market of surfactants reached $23.9 billion in 2008, growing steadily at about 2.8%. By the year of 2010, biosurfactants could capture 10% of the surfactant market, reaching $2 billion in sales (Nitschke et al., 2005). The annual surfactant market in the U.S. is about 7.7 billion pounds, of which 60% is oleoehemical based. These biosurfactants are either derived directly from the vegetable oil refining processes, or from oil seeds, bacteria and yeast by extensive separation processes or enzymatic esterification. There is a large existing surfactants market for phospholipids. The U.S. food industry consumes over 100 million pounds per year of lecithin (soybean phospholipid, an anionic surfactant). These are co-products of soybean and other vegetable oil refining processes.

However, the amount of phospholipids in the initial crude oil is at the most 3% (i.e., 3000 ppm). Also, non-ionic synthetic surfactant consumption in the same market is four times the size of the lecithin market. Non-ionic biosurfactants such as glycolipids, if available in bulk, can potentially replace lecithin. Some of the major glycolipid biosurfactants, rhamnolipids, sophorolipids, and trehalose lipids are produced by microbial fermentation. Rhamnolipids are produced intracellularly by the bacterium *Pseudomonas* sp. Sophorolipids are produced extracellularly by *Candida* sp. Trehalose lipids are cell wall components in *Mycobacteria* and *Gorynebacteria*. These are major toxic components in the cell wall and reduce the permeability of the membranes conferring appreciable drug resistance to the organisms. These fermentation processes typically use hydrocarbons, glucose, vegetable oils as substrates (Gautam and Tyagi, 2006)

Recently the synthesis of biosurfactants has been developed using microbial enzymes. There have been many reports on the synthesis of sugar fatty acid esters from sugars (glucose, fructose and sucrose) and sugar alcohols (glycerol, xylitol and sorbitol) catalyzed by Upases (Kitamoto et al., 2002). In the lipase—catalyzed esterification, which is a dehydration condensation, one of the major difficulties is how to efficiently remove water produced as the reaction progresses or how to properly regenerate the solvent. Several strategies are being used to surmount these problems, namely to perform the reaction under reduced pressure, to use water adsorbents like molecular sieves, or to employ membrane pervaporation techniques (Yahya et al., 1998; Yan et al., 2001). Further, there is a problem with stability and activity of the enzyme, and the solubility of substrates (especially solubility of sugars in organic solvents). An example of the industrial production of glycolipid biosurfactants using the enzyme method is synthesis of a butyl glucoside from maltose and n-butanol by glucose transferase with an annual yield of 240 kg (Bonsuet et al, 1999).

All the existing technologies for producing polar lipids are raw material or cost prohibitive. Other economical alternative feedstocks for glycolipids and phospholipids are mainly algae oil, oat oil, wheat germ oil and vegetable oil. Algae oil typically has 30-85% (w/w) polar lipids depending on the species, physiological status of the cell, culture conditions, time of harvest, and the solvent utilized for extraction. The biosurfactant properties that enable numerous commercial applications also increase the separation costs and losses at every processing step. Because the glycerol backbone of each polar lipid has two fatty acid groups attached instead of three in the neutral lipid triacylglycerol, transesterification of the former may yield only two-thirds of the end product, i.e., esterified fatty acids, as compared to that of the latter, on a per mass basis. Hence, removal and recovery of the polar lipids would not only be highly beneficial in producing high quality biofuels or triglycerides from algae, but also generate value-added co-products glycolipids and phospholipids, which in turn can offset the cost associated with algae-based biofuel production.

Biosurfactant recovery depends mainly on its ionic charge, water solubility, and location (intracellular, extracellular or membrane bound). Examples of strategies that can be used to separate and purify polar lipids in batch or continuous mode include (Gautam et al., 2006): (1) Batch mode: Precipitation (pH, organic solvent), solvent extraction and crystallization; (2) Continuous mode: centrifuging, adsorption, foam separation and precipitation, membranes (tangential flow filtration, diafiltration and precipitation, ultra filtration)

Most of the above listed technologies were utilized in separation and purification of biosurfactants either from fermentation media or vegetable oils. However, exemplary embodiments of the present disclosure utilize a crude algal oil that is similar with a vegetable oil in terms of lipid and fatty acid composition. The differences between algal oil used in exemplary embodiments and vegetable oils used in previous embodiments include the percentage of individual classes of lipids. An exemplary algal crude oil composition is compared with vegetable oil shown in Table 1 below:

| | Algal Crude Oil (w/w) | Vegetable Oil (w/w) |
|---|---|---|
| Neutral lipids | 30-90% | 90-98% |
| Phospholipids | 10-40% | 1-2% |
| Glycolipids | 10-40% | <1% |
| Free fatty acids | 1-10% | <3% |
| Waxes | 2-5% | <2% |
| Pigments | 1-4% | ppm |

In the vegetable oil industry, the product of chemical degumming to remove polar lipids (biosurfactants) retains a lot of the neutral lipid (triglycerides) fraction. This neutral lipid fraction is further removed from the degummed material using solvent extraction or supercritical/subcritical fluid extraction or membrane technology. Of these technologies, membrane technology may eliminate the preliminary chemical degumming step and directly result in polar lipids almost devoid of neutral lipids.

SUMMARY

Embodiments of the present invention relate generally to systems and methods for extracting lipids of varying polarities from an oleaginous material, including for example, an algal biomass. In particular, embodiments of the present invention concern extracting lipids of varying polarities from an algal biomass using a series of membrane filters.

In particular embodiments, the recovery/extraction process can be done on a wet biomass. A major economic advantage of exemplary embodiments results from not having to dry and disrupt the cell. Data on extracting dry algae with many typical solvents (both polar & non polar) do not even come close to the recoveries/fractionations achieved with exemplary embodiments of the exemplary systems and methods. Disruption of wet biomass frequently results in emulsions and component separations are difficult.

Exemplary embodiments may be applied to any algae or non-algae oleaginous material. Exemplary embodiments may use any water-miscible slightly non-polar solvent, including for example, MeOH, EtOH, IP A, Acetone, EtAc, AcN. Specific embodiments may use a green renewable solvent. In exemplary embodiments, extraction and fractionation can be performed in one step followed by membrane-based purification if needed. The resulting biomass is almost devoid of water and can be completely dried with lesser energy than aqueous algae slurry.

Certain embodiments comprise a method of extracting lipids from an' oleaginous material, where the method comprises: providing a plurality of inlet reservoirs and a plurality of separation devices and directing an oleaginous material and a water-soluble solvent through the plurality of inlet reservoirs and the plurality of separation devices. In specific embodiments, each of the plurality of separation devices separates the oleaginous material and the water-soluble solvent into a retentate portion and a diffiisate portion. Particular embodiments also comprise directing the retentate portion to a subsequent inlet reservoir and separation device and recycling the diffusate portion to a prior inlet reservoir.

In specific embodiments, the oleaginous material can be an algal biomass, and in certain embodiments the oleaginous material is wet. In particular embodiments, the water-soluble solvent can be selected from the group consisting of: MeOH, EtOH, IPA, acetone, EtAc, or AcN. In specific embodiments, cells of the oleaginous material may not be dried or disrupted. In certain embodiments, extraction and fractionation of the oleaginous material can be performed in a single step.

In specific embodiments, a first separation device can separate the oleaginous material and the water-soluble solvent into a first retentate portion and a first diffusate portion. In particular embodiments, a second separation device can separate the oleaginous material and the water-soluble solvent into a first retentate portion and a first diffusate portion, where the first retentate portion comprises a higher concentration of polar lipids than the second retentate portion and where the second retentate portion comprises a higher concentration of neutral lipids than the first retentate portion.

In certain embodiments, the neutral lipids can comprise triglycerides. In particular embodiments, the plurality of separation devices can comprise a first separation device and a second separation device. In specific embodiments, the first separation device can separate the oleaginous material and the water-soluble solvent into a first retentate portion and a first diffusate portion, and the second separation device can separate the oleaginous material and the water-soluble solvent into a first retentate portion and a first diffusate portion. In particular embodiments, the first retentate portion can have a higher polarity than the second retentate portion. In certain embodiments, the plurality of separation devices can comprise a plurality of membrane filters. In specific embodiments, the membrane can comprise one or more of the following materials: polyethersulfone (PES), polyamide (PA), polysulforie (PS), polyvinylidene difluoride (PVDF), polyimide (PI), and polyacrylonitrile (PAN). In particular embodiments, the water-soluble solvent can comprise an alcohol. In certain embodiments, the water-soluble solvent can be maintained at a temperature near the boiling point of the water-soluble solvent. In specific embodiments, the water-soluble solvent can be maintained at a temperature between 40 and 70 degrees Celsius.

In particular embodiments, the plurality of separation devices can comprise: a first separation device configured to separate particles larger than 100 um from particles smaller than 100 um; a second separation device configured to separate particles larger than 10 urn from particles smaller than 10 um; and a third separation device configured to separate particles larger than 1 um from particles smaller than 1 (um. In specific embodiments, the plurality of inlet reservoirs can be maintained at a pressure of approximately 1-10 bars. In certain embodiments, the diffusate portion can be directed to a recycle reservoir and before being recycled to the prior inlet reservoir. Particular embodiments can comprise a recycle pump configured to recycle the diffiisate portion to the prior inlet reservoir.

Certain embodiments can comprise a system for extracting lipids from an oleaginous material, where the system comprises: a first, second, and third inlet reservoir, and a transport mechanism configured to move the oleaginous material and a water-soluble solvent from the first inlet reservoir to the second inlet reservoir, and from the second inlet reservoir to the third inlet reservoir. Particular embodiments may also comprise a first separation device between the first and second inlet reservoirs, where the first separation device is configured to separate the oleaginous material and the water-soluble solvent into a first retentate portion and a first diffusate portion. Specific embodiments can also comprise a second separation device between the second and third inlet reservoirs, where the second separation device is configured to separate the oleaginous material and the water-soluble solvent into a second retentate portion and a second diffusate portion.

Certain embodiments of the system can also comprise a first recycle pump configured to pump the first difrlisate portion to the first inlet reservoir, and a second recycle pump configured to pump the second diffusate portion to the second inlet reservoir. In particular embodiments, the first and second separation devices each comprise a membrane filter. In specific embodiments, the membrane filter of the first separation device can be configured to separate particles larger than 100 um from particles smaller than 100 urn. In certain embodiments, the membrane filter of the second separation device can be configured to separate particles larger than 10 urn from particles smaller than 10 um.

In particular embodiments of the system, the membrane filters of the first and second separation devices can comprise one or more of the following materials: polyethersulfone (PES), polyamide (PA), polysulfone (PS), polyvinylidene difluoride (PVDF), polyimide (PI), and polyacrylonitrile (PAN). In certain embodiments, the first retentate portion can comprise a higher concentration of polar lipids than the second retentate portion, and the second retentate portion comprises a higher concentration of neutral lipids than the first retentate portion. In particular embodiments, the water-soluble solvent can comprise an alcohol. In specific embodiments, the water-soluble solvent can be maintained at a temperature near the boiling point of the water-soluble solvent. In certain embodiments, the water-soluble solvent can be maintained at a temperature between 40 and 70 degrees Celsius.

It is contemplated that any embodiment discussed in this specification can be implemented with respect to any method or system of the invention, and vice versa. Furthermore, systems of the invention can be used to achieve methods of the invention.

The term “conduit” or any variation thereof, when used in the claims and/or specification, includes any structure through which a fluid may be conveyed. Non-limiting examples of conduit include pipes, tubing, channels, or other enclosed structures.

The term “reservoir” or any variation thereof, when used in the claims and/or specification, includes any body structure capable of retaining fluid. Non-limiting examples of reservoirs include ponds, tanks, lakes, tubs, or other similar structures.

The term “about” or “approximately” are defined as being close to as understood by one of ordinary skill in the art, and in one non-limiting embodiment the terms are defined to be within 10%, preferably within 5%, more preferably within 1%, and most preferably within 0.5%.

The terms “inhibiting” or “reducing” or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF EXEMPLARY EMBODIMENTS

For solvent extraction of oil from algae the best case scenario is a solvent which selectively extracts triacylglycerols (TAG) and leaving all polar lipids and non-TAG neutral lipids such as waxes, sterols in the algal cell with high recoveries. The second option would be selectively extract polar lipids and then extract purer neutral lipids devoid of polar lipids, resulting in high recovery. The last option would be to extract all the lipids and achieve very high recovery in one or two steps.

Figure 1:
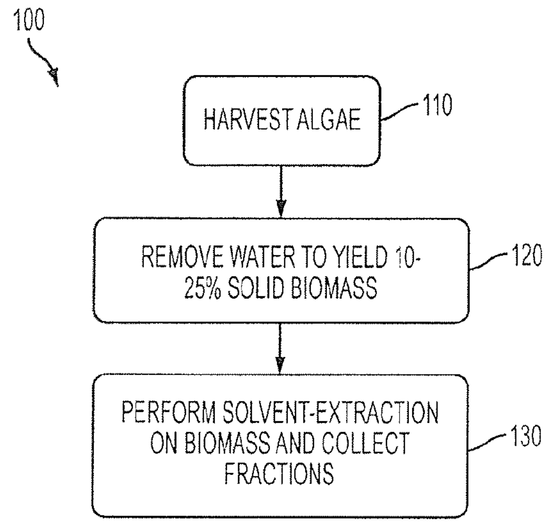
FIG. 1 is a flowchart of steps involved in a method according to an exemplary embodiment of the present disclosure.
Figure 1:
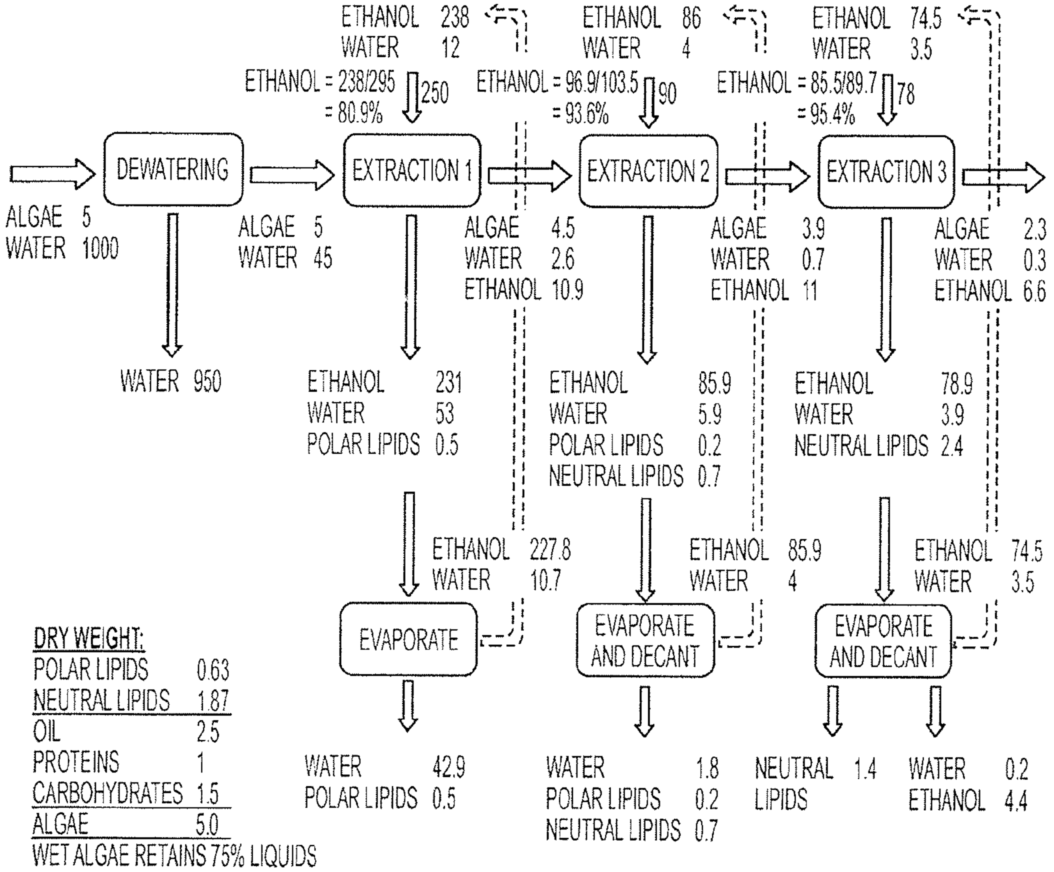

Referring now to FIG. 1, a flowchart 100 provides an overview of the steps involved in exemplary embodiments of methods used in the fractionation and purification of lipids from an algae-containing biomass. In a first step 110, algal cells are harvested. In a subsequent step 120, water is removed from alga cells to yield a 10-25% solid biomass. In step 130, a solvent-based extraction is performed on the biomass and the fractions are collected. Finally, membrane filtration may be performed in a step 140 to separate out smaller lipid components.

The algae biomass when harvested in step 110 typically consists of 1-5 g/L of total solids. The biomass can be de-watered in step 120 using the techniques including, for example, dissolved air floatation, membrane filtration, flocculation, sedimentation, or centrifuging. The de-watered algae biomass resulting from step 120 typically consists of 10-30% solids. This biomass can then be extracted with water-soluble solvents (e.g., alcohols), in a multistage countercurrent solvent extraction process segregating the fractions at each stage.

Figure 2:
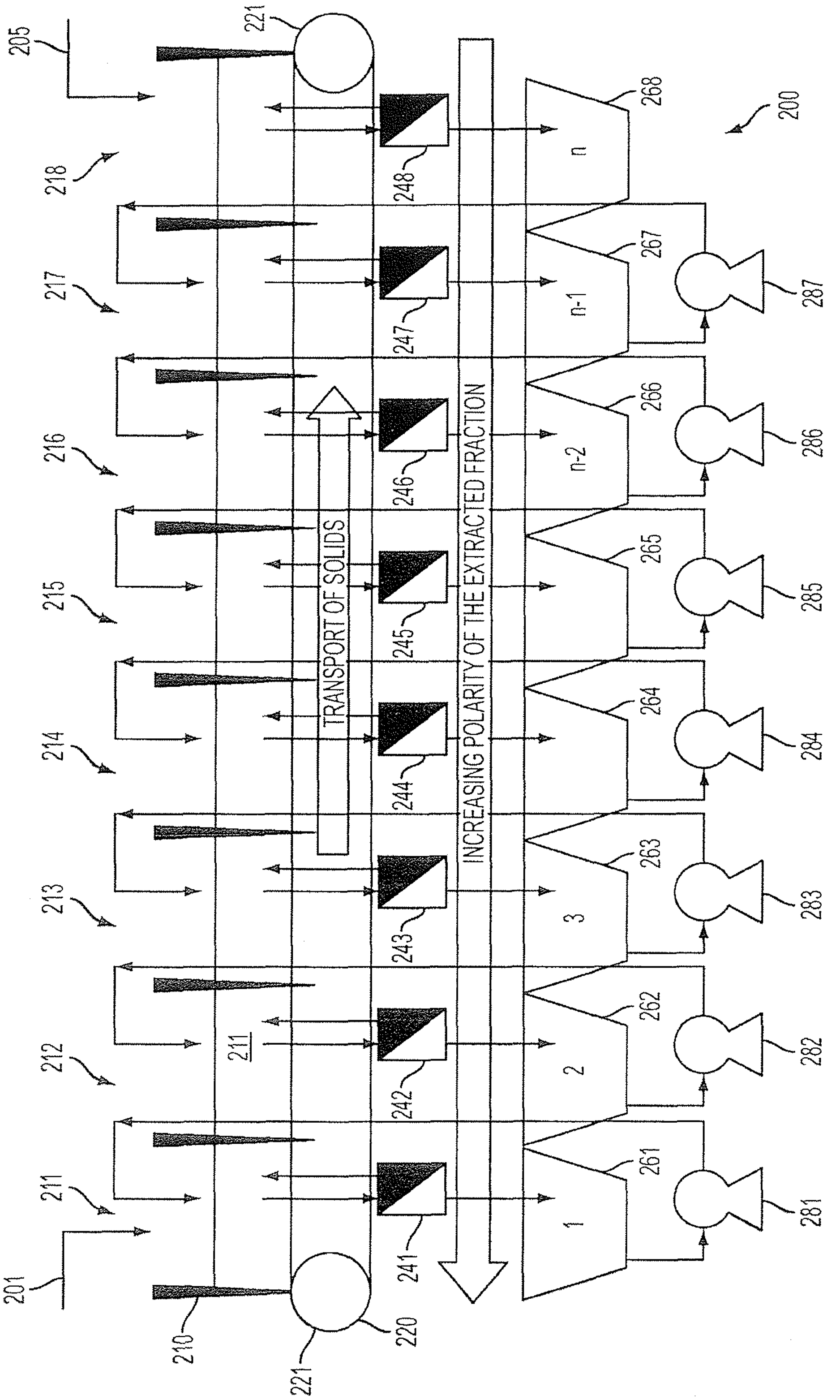
FIG. 2 is a schematic diagram of an exemplary embodiment of an extraction system according to the present disclosure.

Referring now to FIG. 2, a schematic diagram of an exemplary embodiment of an extraction system 200 one is provided. The wet or dry algal biomass is transported on a moving belt. The solvent for extraction is recirculated from a storage tank assigned to each biomass slot position. The extraction mixture is filtered returning the biomass solids back into the slot and the extract into the storage tank. The solids on the belt move periodically based on the residence time requirement for extraction. The extracts in each storage tanks may either be replenished at saturation or continuously replaced by fresh solvent. This would also reduce the downstream processing time and costs drastically. This embodiment comprises a primary reservoir 210, a transport mechanism 220, a plurality of separation devices 240 (e.g., membrane filtration devices), a plurality of extraction reservoirs 260, and a plurality of recycle pumps 280. In this embodiment, primary reservoir 210 is divided up into a plurality of inlet reservoirs 211-218.

During operation, algal biomass (indicated by arrow 201) is placed a first inlet reservoir 211 near a first end 221 of transport mechanism 220. In addition, solvent (indicated by arrow 205) is placed into inlet reservoir 218 near a second end 222 of transport mechanism 220. Transport mechanism 220 directs the algal biomass along transport mechanism 220 from first end 221 towards second end 222. As the algal biomass is transported, it passes through the plurality of separation devices 241-248 and is separated into fractions of varying polarity. The diffusate portions that pass through separation devices 241-248 are directed to reservoirs 261-268.

For example, the diffusate portion of the algal biomass that passes through the first separation device 241 (e.g., the portion containing liquid and particles small enough to pass through separation device 241) is directed to the first reservoir 261. From first reservoir 261, the diffusate portion can be recycled back to first inlet reservoir 201. The retentate portion of the algal biomass that does not pass through first separation device 241 can then be directed by transport mechanism 220 to second inlet reservoir 212 and second separation device 242, which can comprise a finer separation or filtration media than the first separation device 241.

The segment of the diffusate portion that passes through second separation device 242 can be directed to second reservoir 262, and then recycled back to second inlet reservoir 212 via recycle pump 282. The retentate or extracted portion of the algal biomass that does not pass through second separation device 242 can be directed by transport mechanism 220 to third inlet reservoir 213. This process can be repeated for inlet reservoirs 213-218 and separation devices 243-248 such that the extracted portions at each stage are directed to the subsequent inlet reservoirs, while the diffusate portions are directed to the recycle reservoirs and recycled back to the current inlet reservoir.

In exemplary embodiments, the last fraction extracted will be with the purest solvent and the first fraction with a saturated solvent. The process therefore extracts components in the order of decreasing polarity with the fraction. The function of the first fraction is to remove the residual water and facilitate the solvent extraction process. The fractions that follow are rich in polar lipids, while the final fractions are rich in neutral lipids.

Figure 3:
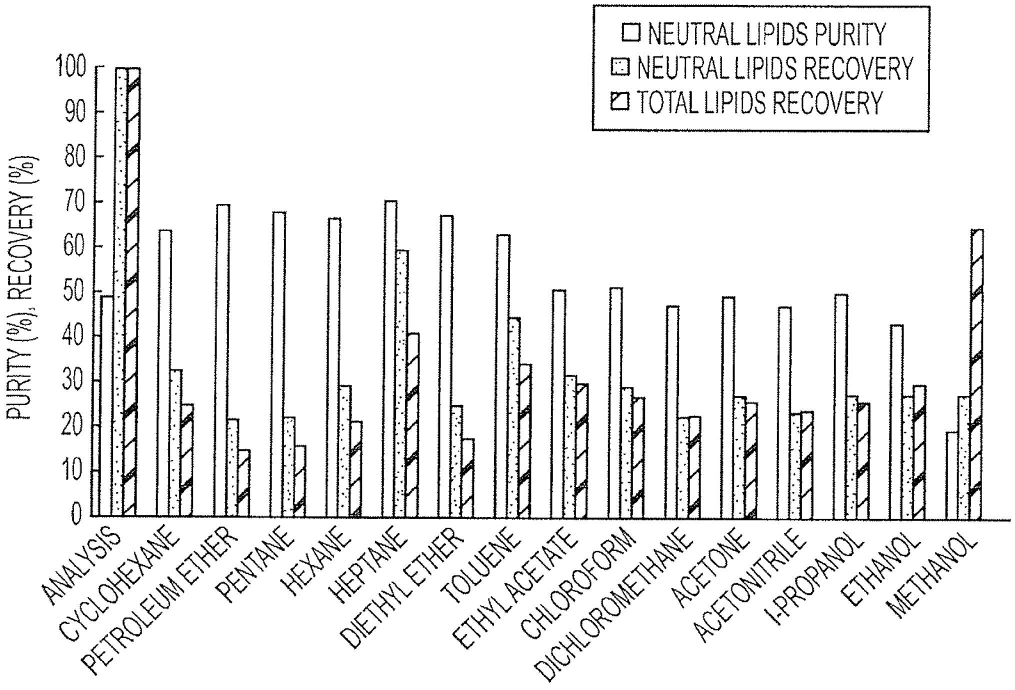
FIG. 3 is a comparative chart showing Sohxlet extraction of freeze dried algae biomass using an array of solvents encompassing the complete polarity range showing maximum non-disruptive algae oil extraction efficiency and the effect of polarity on the polar and non-polar lipids extraction.

The solvent selection and the theory of fractionation based on polarity were developed by extensive analysis of solvents and the effect on extraction using the Sohxlet extraction process. Sohxlet extraction system was utilized for rapid screening solvents for lipid class selectivity and recovery. Solvents from various chemical classes encompassing a wide range of polarities such as alkanes, cycloalkane, alkyl halides, esters, ketones, were tested. The lipid content and composition of the biomass was tested in triplicates using the standard methods in our lab prior to the Sohxlet extraction. The total lipids in the biomass utilized were 22.16% (dry weight basis) and the neutral lipid content was 49.52%. The results from the Sohxlet extraction are shown in FIG. 3. We can achieve about 60-70% purity of neutral lipids and 15-45% of total lipids recovery depending on the chain length of the alkane without disruption and solvent extraction. The longest chain alkane tested, heptane showed 60% neutral lipids recovery and 42% recovery of total lipids. However, the maximum neutral lipids purity was less than 70%. Thereby indicating that use of single solvent for extraction of neutral lipids selectively may not be feasible. The lower carbon alcohols were more selective towards polar lipids. The neutral lipids purity was 22% for methanol and 45% for ethanol. Isopropyl alcohol did not show any selectivity to lipids class and the neutral lipids purity was 52%. Methanol specifically could recover 67% of the total lipids and more than 90% of the polar lipids. Thereby, methanol is a perfect proponent for our second option of selectively extracting polar lipids prior to extracting the neutral lipids using heptane or hexane. Other solvent classes tested did not show any selectivity towards lipids class since the neutral lipids purity was close to 49% (resembling the lipid composition in the biomass) and the total lipids recovery ranged from 15 to 35%, rendering these solvents not being suitable for a specific lipids class extraction or total lipids extraction.

The results from the Sohxlet analysis were confirmed using the standard bench scale batch solvent extraction apparatus. The solvents selected were methanol for the first step to recover polar lipids and petroleum ether in the second step to recover neutral lipids. All the extractions were performed with a 1:10 solid: solvent ratio and with each step for 1 hour. The methanol extractions were performed at different temperatures as discussed below and the petroleum ether extraction was performed close to the boiling point of the solvent at 35 C throughout the following set of experiments. Petroleum ether was chosen because of its high selectivity to neutral lipids, low boiling point and the product quality observed after extraction. From FIG. 4 (*a*) we can observe that the neutral lipid purity in subsequent extraction after a methanol extraction step at 65° C. is over 80%. We can also see that the methanol extraction performed near the boiling point can significantly enhance the purity of the neutral lipids in the subsequent extraction.

Figure 4A:
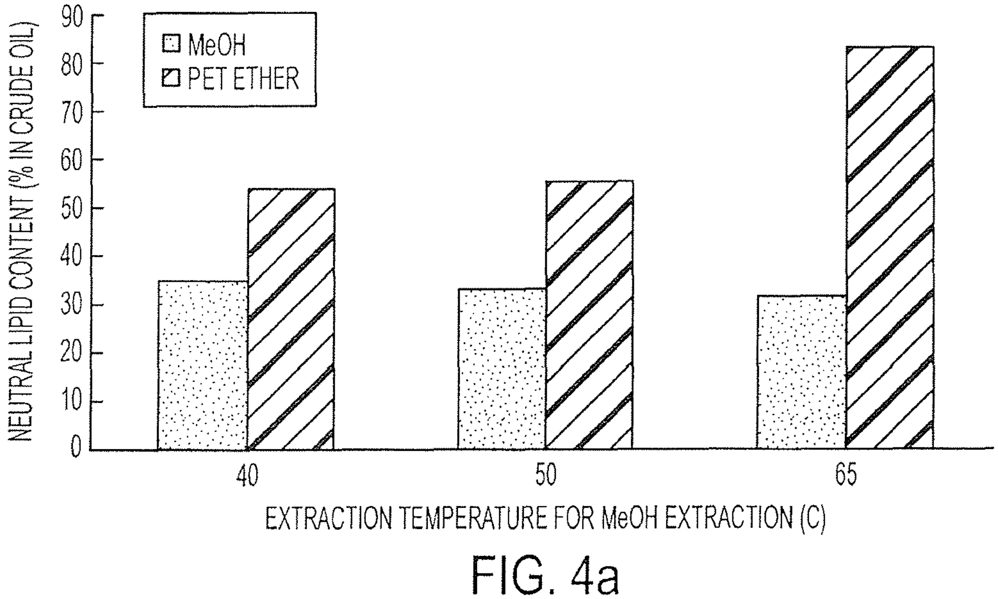
FIG. 4 is a chart showing neutral lipids (a) Purity (b) Recovery in the two step solvent extraction process using methanol and petroleum ether at three different temperatures.
Figure 4B:
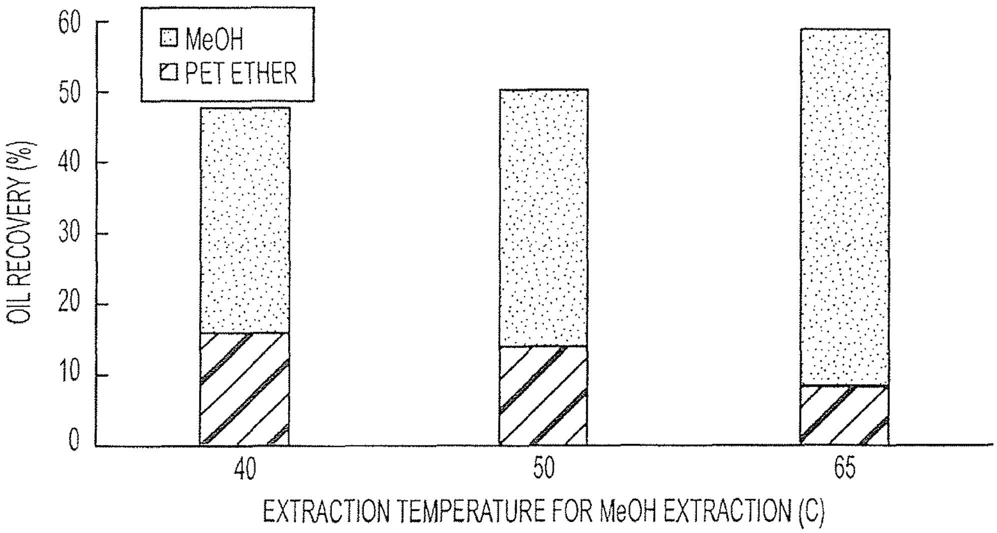

We can see from FIG. 4(*b*) that the total neutral lipid recovery is low and there is a significant amount of neutral lipid loss in the first step.

Figure 5A:
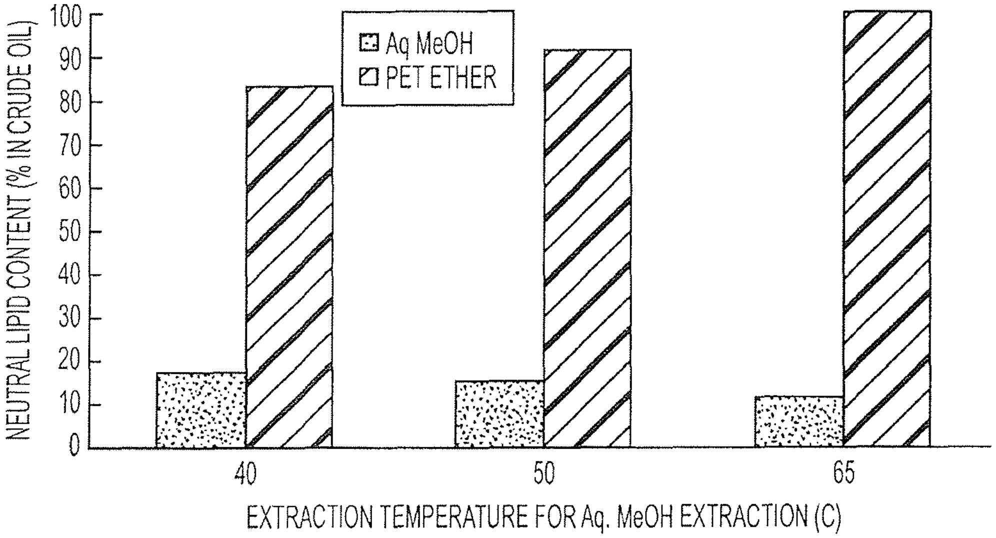
FIG. 5 is a chart showing neutral lipids (a) Purity (b) Recovery in the two step solvent extraction process using aqueous methanol and petroleum ether at three different temperatures.
Figure 5B:
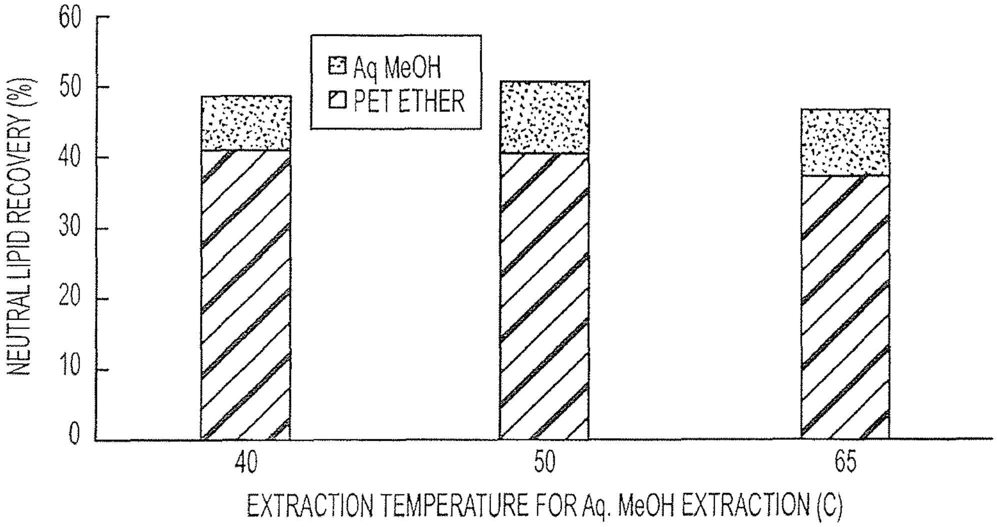
Figure 7:
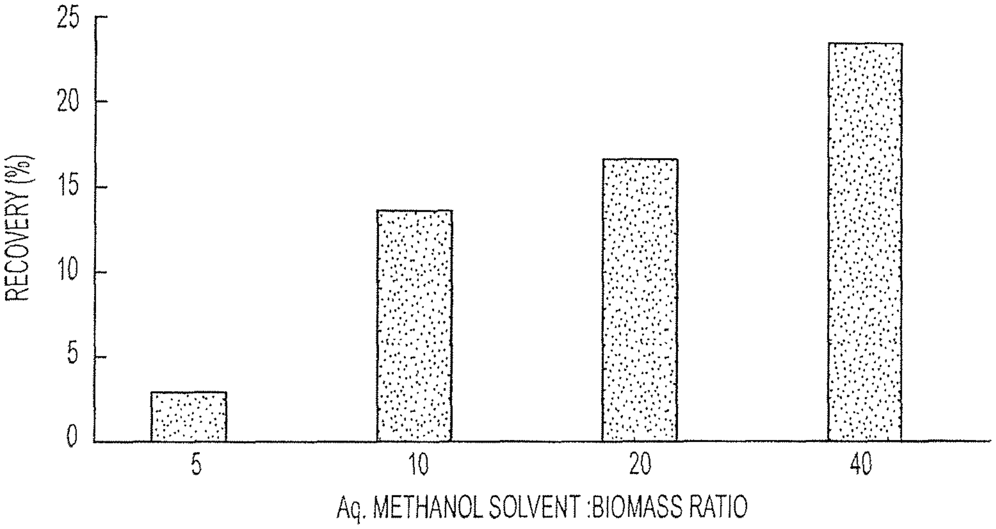
FIG. 7 is a chart showing the effect of solvents solid ratio on lipid recovery.

To minimize the loss of neutral lipids in the methanol extraction step, the polarity of the solvent can be increased by adding water to the solvent. The results are shown in FIG. 5. From FIG. 5(*a*) we can observe that the neutral lipid purity is much higher in the petroleum ether extraction than the previous case. Also, the loss of neutral lipids in the aqueous methanol extraction step is much lower than pure methanol. We also observed that higher temperature for methanol extraction improved the neutral lipid purity but slightly decreased the recovery in the subsequent step. FIG. 7 shows the effect of solvent solid ratio on the extraction recovery. Given the lower solubility of lipids in methanol compared to other commonly used oil extraction solvents such as hexane, we observed a drastic increase in the total lipid recovery by increasing the solvent to solid ratio.

Figure 6:
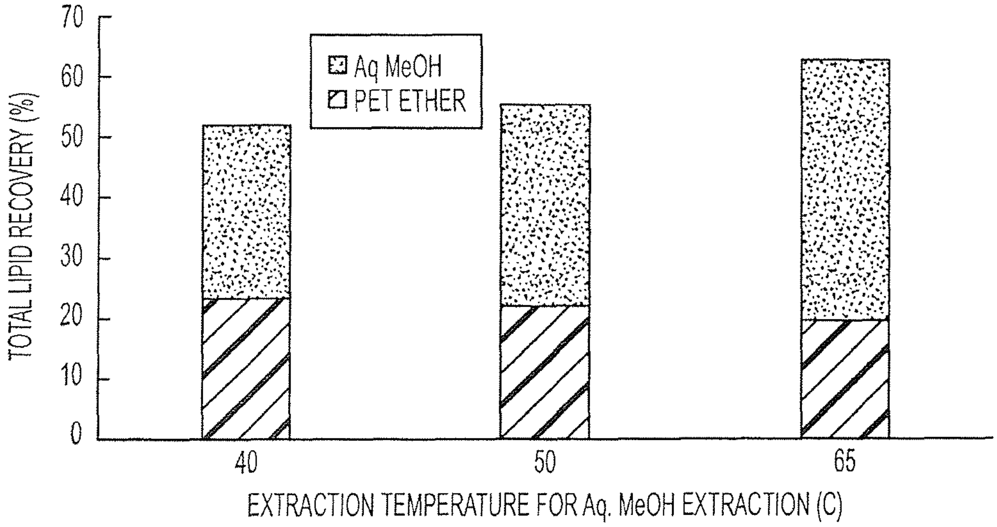
FIG. 6 is a chart showing lipid recovery in the two step solvent extraction process using aqueous methanol and petroleum ether at three different temperatures.

In exemplary embodiments, the extraction is effective close to the boiling point of the solvent used. At such temperatures, vapor phase penetration of the solvent into the algal cells is faster due to lesser mass transfer resistance. If the extraction temperature is allowed to significantly exceed the boiling point of the solvent, the solvent-water system can form an azeotrope. Thus maintaining the system at the boiling point of solvent would create enough vapors to enhance the extraction and not the capital costs. In addition, the solubility of oil is higher at higher temperatures, which can further increase the effectiveness at temperatures close to the solvent boiling point. FIG. 6 shows the total lipid recovery in the aqueous methanol-petroleum ether extraction scheme. Although performing the methanol extraction near its boiling temperature slightly decreases the neutral lipid recovery as observed in FIG. 5*b*, it enhances the total lipid recovery.

In exemplary embodiments, the solvent-to-solid ratio for the extraction is between 3-5 based on the dry weight of the solids in the biomass. The residual algal biomass is rich in carbohydrates (e.g., starch) and can be used as a feed stock to produce the solvent used for extraction.

Figure 9:
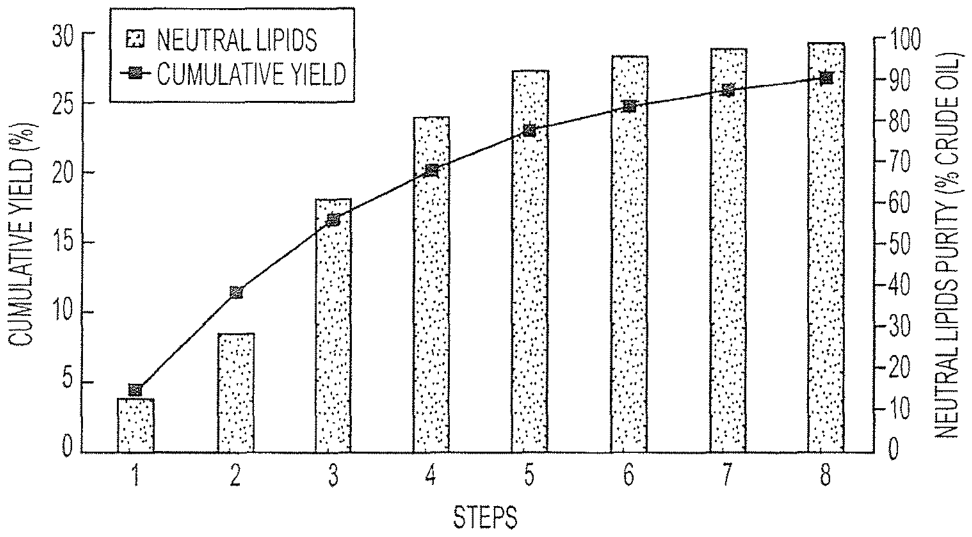
FIG. 9 is a chart showing the effect of multiple step methanol extractions on the cumulative total lipid yield and the neutral lipids purity. (112 g wet biomass (25.6% dry weight) extracted with 350 mL pure methanol for 10 minutes at 160 W irradiance power in each step).
Figure 10:
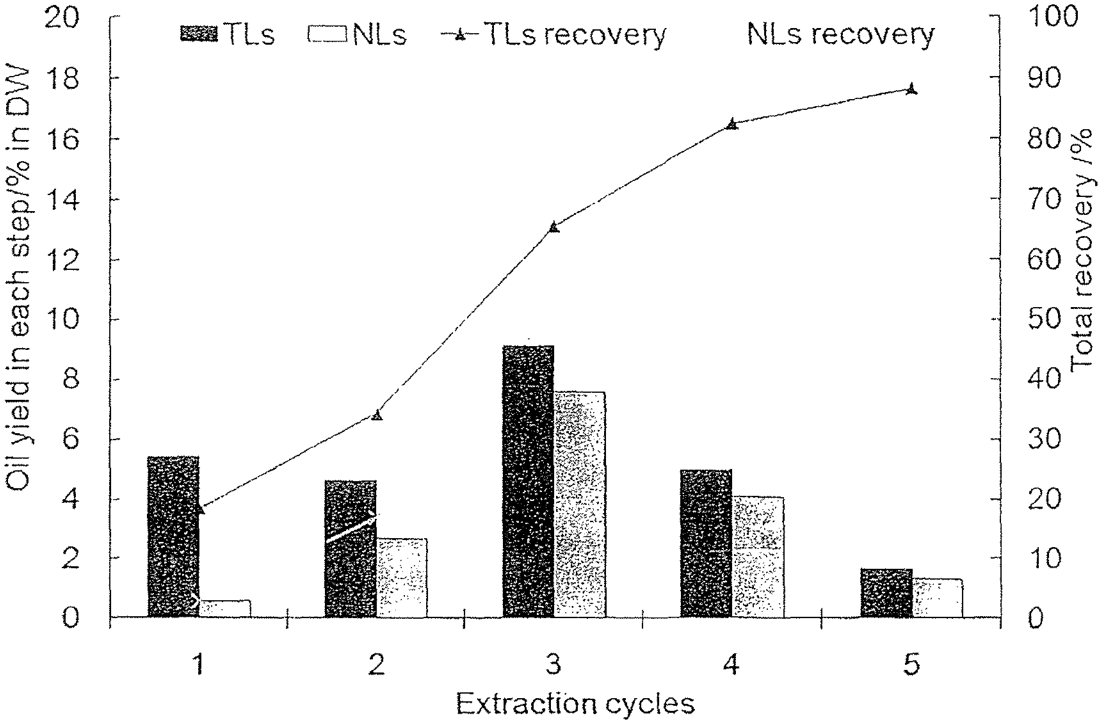
FIG. 10 is a chart showing the cumulative recovery of lipids using wet biomass and ethanol.

From FIG. 9 we can observe that it is possible to get high purity neutral lipid once the polar lipids are all extracted. In this case we can get 5% yield with over 90% neutral lipids purity in extraction steps 5 through 8. Also, based on the boiling point of the extraction mixture, we can assert that most of the water in the biomass is completely extracted in the first extraction step along with carbohydrates, proteins and metals. From FIG. 10 we can observe faster recovery of lipids using ethanol and wet biomass. The number of steps for over 80% total lipids recovery has been reduced from about 9 steps using methanol to 4 steps using ethanol. This increase in recovery may be attributed to greater lipids solubility in ethanol compared to methanol. Also, the boiling point of the aqueous ethanol is higher than aqueous methanol facilitating 5 further recovery of lipids. The main advantages of this process would consist of the productivity of ethanol using the residual biomass after oil extraction, utilization of ethanol in the oil extract for transesterification. Further from FIG. 10 we can observe that the initial fractions are non-lipid rich followed by the lipid rich fractions and finally the neutral lipid fractions. Hence with a proper design of the extraction apparatus, one can recover all the three fractions in one process.

Figure 8:
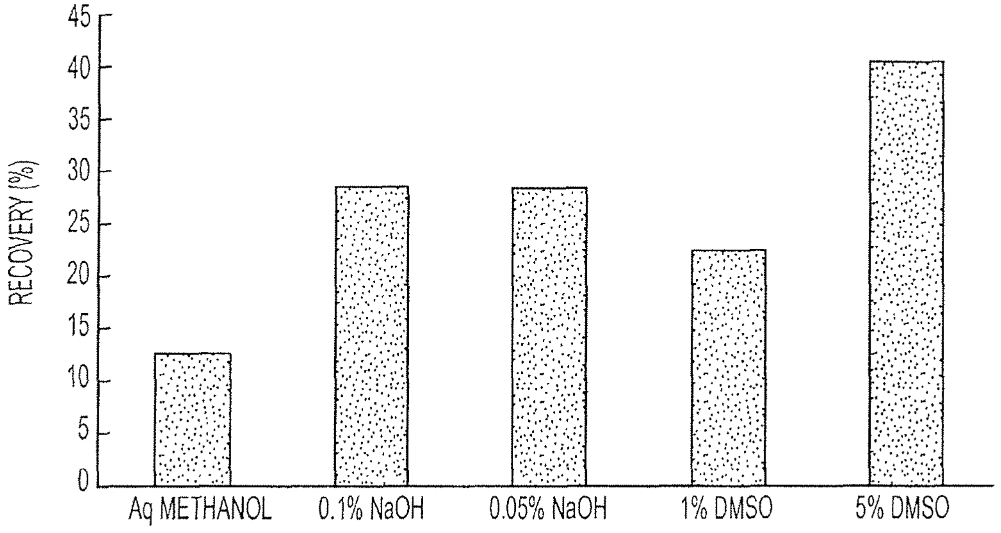
FIG. 8 is a chart showing the effect of additives on a single step extraction recovery of aqueous methanol on dry biomass.
Figure 11:
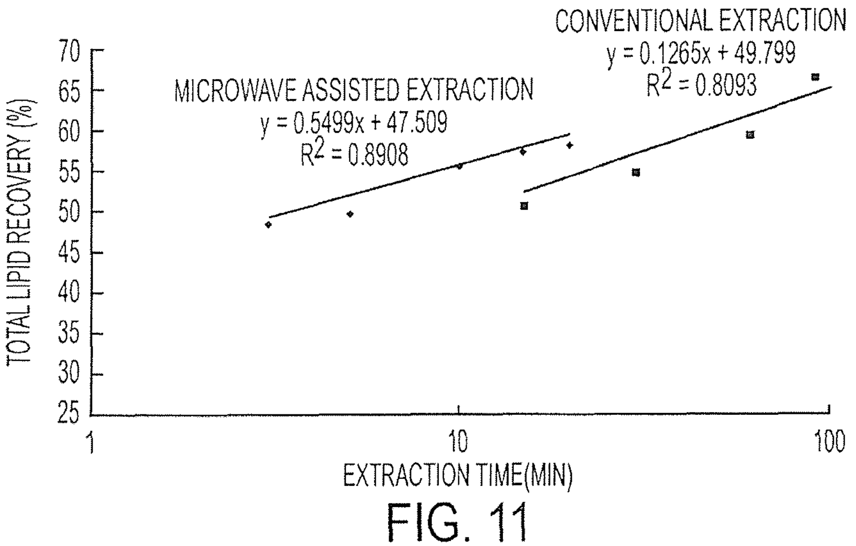
FIG. 11 is a chart showing comparison of the extraction times of the microwave assisted extraction and conventional extraction systems.

Another aspect of the current invention is the comparison of using microwave for extraction and the conventional extraction methods. FIG. 11 (*a*) is log-normal plot of the extraction time and total lipid recovery for the microwave and the conventional systems. As we can see the microwave system reduces the extraction time by 10 fold; Also from the slope of the curve we can see that the extraction rate for the microwave assisted system is about 4 times greater than that of the conventional method. However, the net recovery is higher for the conventional method due to higher recoveries of the polar lipids. Based on these results we have the best conditions for extraction of dry algal biomass using solvents with and without microwave assistance. Hence, we may need to modify the algal cells prior to extraction to enhance the productivity and efficiency. In this direction we performed a small experiment comparing the effect of adding a base or another organic solvent in small amounts to chance the surface properties and enhancing extraction. As we can see from FIG. 8, an addition of 5% DMSO increases the recovery 3 times. This may translate into reducing all the methanol extraction steps dramatically. However, these solution used in the above experiments may not be the best case scenario on a larger scale due to the formation of azeotropes. From our previous data we know that methanol is the best single solvent for extraction of all lipids from algae. Hence, we performed a single solvent multiple step extraction to study the possible one solvent microwave extraction system.

Figure 12:
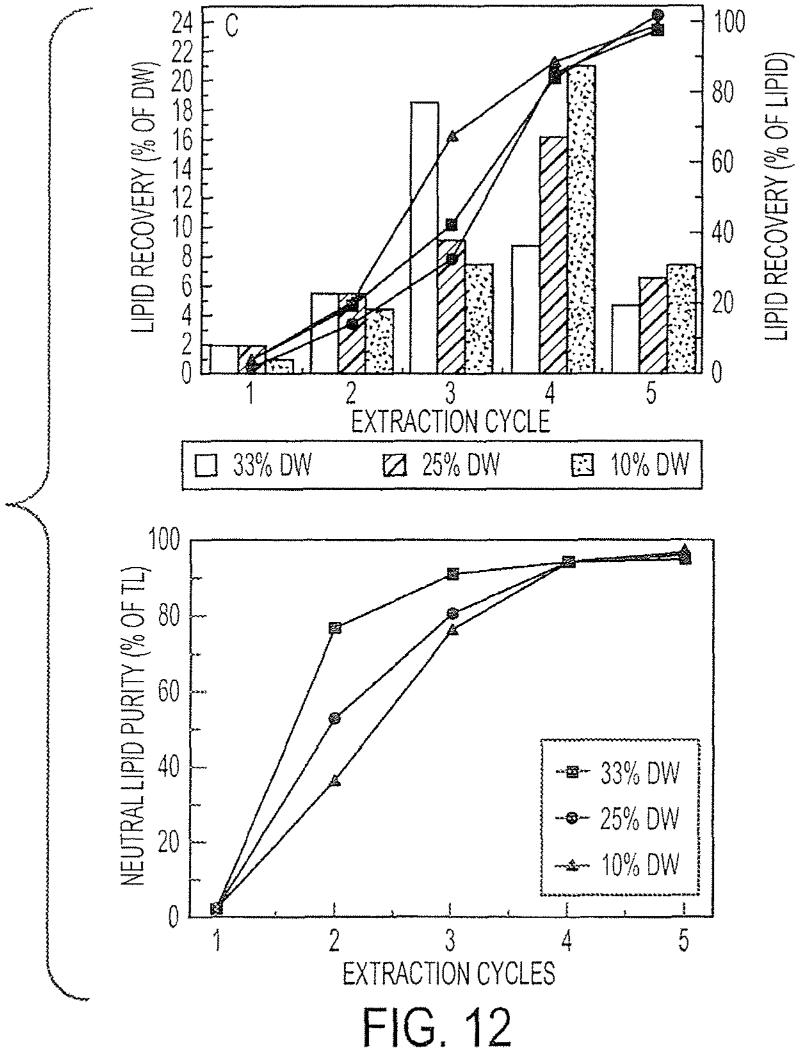
FIG. 12 is a chart showing the effect of moisture content on extraction (Table 1: Comparison of algal oil to vegetable oil).

Moisture content is another important parameter of algae which will obviously influence the oil extraction performance. Algae sample with dry algae content at 10%, 25%, 33% were used to investigate the influence of moisture on extraction performance. As indicated in the FIG. 12, the lipid evolution profile were largely influenced by the moisture content in the starting algae, when the dry weight decreased from 33% to 25% and 10%, the maximum lipid recovery step change to fourth extraction cycle from the third one. However, the overall lipid recovery from these three algae samples was quite similar, all above 95% of the reference value. The neutral lipid percentage in the crude extract of these three algae is shown in FIG. 12. It can be found that the neutral lipid percentage in the first three steps is decreased as the dry weight algae decreased, while no difference was found in the last two cycles. The difference in oil extraction performance can again be explained from the difference of the solvent system. When higher moisture content of the algae was used, the ethanol concentration in the aqueous ethanol mixture was much lower, and consequently the neutral lipid percentage in the crude extract was also lower. It was reported that further dewater from algae paste with 90% water was a very energy intensive process. Hence it is interesting to see the overall lipid recovery was not obviously influenced even starting from the algae paste with 90% water, which means a cost much more acceptable dewater process is enough for our extraction system.

In exemplary embodiments, the polar lipids rich fraction is further processed using membranes to separate smaller components such as triglycerides, fatty acids, carotenoids. The ability of polar lipids to aggregate can also been used to retain them on high-molecular-weight-cutoff membranes. Phospholipids are amphoteric molecules that can form reverse micelles in the medium with a molar mass above 20 kDa and molecular size from 20 to 200 nm (Koseoglu, 2002). Solvent stable ultrafiltration (UF) (e.g., filtration of particles greater than approximately 10 fun) or nanofiltration (NF) (e.g., filtration of particles greater than approximately 1 nm) membranes can be made of polyethersulfone (PES), polyamide (PA), polysulfone (PS), polyvinylidene difluoride (PVDF), polyimide (PI), polyacrylonitrile (PAN) or suitable inorganic materials (Cheryan, 1988). In exemplary embodiments, the separation is performed at low to moderate pressures (e.g., 1-10 bar), and the temperatures can be maintained between 40-70 C to reduce the viscosity of the lipids increasing the flux. In specific embodiments,—greater than 90% rejection can be observed based on the membrane selected.

In exemplary embodiments, the membrane separation results in a polar lipids fraction that is over 90% pure and is highly concentrated, which can minimize the additional steps to remove the solvent from the fraction. The fraction rich in neutral lipids {e.g., triglycerides) and can be further used in various applications such as production of biofoels, food and feed, etc.

Example for Extraction:

In one example, green microalga Scendesmus Dimorphus (SD) biomass samples with different lipid contents harvested from outdoor panel photobioreactor were used. Algal samples, after removal of the bulk water by centrifugation, were kept as 3-5 cm algae cake at −80 degrees refrigerator until use. Pre-calculated amount of wet algal biomass (15 g dry algae weight equivalent), 90 ml ethanol solvent was added into a three-neck flask equipped with condensate, mechanical stirring and thermocouple. The mixture was reflux for 10 min under microwave irradiance or Ih with electronic heating, respectively. After reflux time achieves the set value, the mixture was cooled down to room temperature, and separated into crude extract and residual by filtration. The total lipids of algal samples were analyzed in a chloroform-methanol-water system according to Bligh and Dyer's method (ref) and used as reference for the lipid recovery calculation. Total lipids were further separated into neutral lipids and polar lipids by column chromatography using silica gel (60-200 mesh) (Merck Corp., Germany) as previously described: six volumes of chloroform to collect the neutral lipid class and 6 volumes of methanol to collect the polar lipids. Each lipid fraction was transferred into a pre-weighed vial, initially evaporated at (30° C.) using a rotary evaporator (Biichi, Switzerland) and then dried under high vacuum. The dried residuals were placed under nitrogen and then weighed. Fatty acid profile of lipids were quantified by GC-MS after derivatization into fatty acid methyl esters using heptadecanoic acid (C17:0) as the internal standard.

REFERENCES

The following references are herein incorporated by reference in their entirety:

U.S. Pat. No. 4,062,882
U.S. Pat. No. 4,787,981
U.S. Pat. No. 5,374,657
U.S. Pat. No. 5,440,028
U.S. Pat. No. 5,545,329
U.S. Pat. No. 7,148,366
U.S. Patent Publication No. 2002/0209493
Rossignol et al, Aquacultural Engineering, 20:191-208, 2009.

de Morais Coutinho et al., Food Res. Internatl., 42:536-550, 2009.
Huang et al., Applied Energy, 1-8, 2009.
Koris and Vatai, Desalination, 148:149-153, 2002.
Mata et al., m: Renewable and Sustainable Energy Reviews, RSER-757:1-16, 1009.
Rhodes, Science Progress, 92(1):39-90, 2009.
Amin, Energy Conyers. Manage., 50:1834-1840, 2009.
Catchpole et al., J. of Supercritical Fluids, 47:591-597, 2009.
Borowitzka, M. A. (1999). Commercial production of microalgae: ponds, tanks, tubes, and fermenters. *J Biotechnol* 70, 313-321.
Chisti, Y. (2007). Biodiesel from microalgae. *Biotechnol Adv* 25, 294-306.
Daigger, G. T, B. E. Rittmann, S. S. Adham, and G. Andreottola" (2005). Are membrane bioreactors ready for widespread application? *Environ. Sci. Technol.* 39: 399A-406A.
Rittmann, B. E. (2008). Opportunities for renewable bioenergy using microorganisms. *Biotechnol. Bioengr.* 100: 203-212.
Rittmann, B. E. and P. L. McCarty (2001). *Environmental Biotechnology: Principles and Applications*. McGraw-Hill Book Co., New York.

What is claimed is:

1. A method of extracting lipids from an oleaginous material, the method comprising:

de-watering an oleaginous material;

mixing the de-watered oleaginous material with a water-soluble solvent;

heating the oleaginous material and the water-soluble solvent;

providing a plurality of inlet reservoirs and a plurality of separation devices;

directing the oleaginous material and the water-soluble solvent through the plurality of inlet reservoirs and the plurality of separation devices, wherein each of the plurality of separation devices separates the oleaginous material and the water-soluble solvent into a retentate portion and a diffusate portion;

directing the retentate portion to a subsequent inlet reservoir and separation device; and recycling the diffusate portion to a prior inlet reservoir;

wherein a first separation device separates the oleaginous material and the water-soluble solvent into a first retentate portion and a first diffusate portion;

wherein a second separation device separates the oleaginous material and the water-soluble solvent into a second retentate portion and a second diffusate portion;

wherein the first diffusate portion comprises a higher concentration of proteins than the second diffusate portion; and wherein the second diffusate portion comprises a higher concentration of lipids than the first diffusate portion.

2. The method of claim 1, wherein the oleaginous material is de-watered using a technique selected from dissolved air floatation, membrane filtration, flocculation, sedimentation, and centrifugation.

3. The method of claim 1, wherein the mixture is heated under microwave irradiance.

4. The method of claim 1, wherein the mixture is heated by an electronic heating means.

5. The method of claim 1, wherein the oleaginous material is an algal biomass.

6. The method of claim 1, wherein the oleaginous material is dry.

7. The method of claim 1, wherein the water-soluble solvent is selected from the group consisting of methanol, ethanol, isopropanol, acetone, ethyl acetate and acetonitrile.

8. The method of claim 1, wherein extraction and fractionation of the oleaginous material is performed in a single step.

9. The method of claim 1, wherein the oleaginous material and the water-soluble solvent are further admixed with a base.

10. The method of claim 9, wherein the lipids comprise triglycerides.

11. The method of claim 1, wherein:

the plurality of separation devices comprises a first separation device and a second separation device;

the first separation device separates the oleaginous material and the water-soluble solvent into a first retentate portion and a first diffusate portion; and the second separation device separates the oleaginous material and the water-soluble solvent into a first second retentate portion and a first second diffusate portion;

wherein the first diffusate portion has a higher polarity than the second diffusate portion.

12. The method of claim 1, wherein the plurality of separation devices comprises a plurality of membrane filters.

13. The method of claim 1, wherein the membranes comprise one or more of the following materials: polyethersulfone (PES), polyamide (PA), polysulfone (PS), polyvinylidene difluoride (PVDF), polyimide (PI), and polyacrylonitrile (PAN).

14. The method of claim 1, wherein the water-soluble solvent comprises an alcohol.

15. The method of claim 1, wherein the water-soluble solvent is maintained at a temperature near the boiling point of the water-soluble solvent.

16. The method of claim 1, wherein the plurality of separation devices comprises:

a first separation device configured to separate particles larger than 100 μm from particles smaller than 100 μm;

a second separation device configured to separate particles larger than 10 μm from particles smaller than 10 μm; and a third separation device configured to separate particles larger than 1 μm from particles smaller than 1 μm.

17. The method of claim 1, wherein the plurality of inlet reservoirs are maintained at a pressure of approximately 1-10 bars.

18. The method of claim 1, wherein the diffusate portion is directed to a recycle reservoir before being recycled to the prior inlet reservoir.

19. The method of claim 1, further comprising a recycle pump configured to recycle the diffusate portion to the prior inlet reservoir.

* * * * *